United States Patent [19]

Carrico et al.

[11] 4,259,232
[45] Mar. 31, 1981

[54] FLAVIN ADENINE DINUCLEOTIDE-LABELED PROTEIN AND POLYPEPTIDE CONJUGATES

[75] Inventors: Robert J. Carrico; That T. Ngo, both of Elkhart, Ind.

[73] Assignee: Miles Laboratories, Inc., Elkhart, Ind.

[21] Appl. No.: 87,521

[22] Filed: Oct. 23, 1979

[51] Int. Cl.³ .................. C07G 7/00; C07C 103/52
[52] U.S. Cl. ..................... 260/112 R; 260/112.5 R
[58] Field of Search ................ 260/112.5 R; 112 R

[56] References Cited
FOREIGN PATENT DOCUMENTS

| 841179 | 4/1975 | Belgium | 260/112.5 R |
| 1548741 | 4/1975 | United Kingdom | 260/112.5 R |
| 1552607 | 4/1975 | United Kingdom | 260/112.5 R |

Primary Examiner—Delbert R. Phillips
Attorney, Agent, or Firm—Andrew L. Klawitter

[57] ABSTRACT

Flavin adenine dinucleotide-labeled conjugates of the formula:

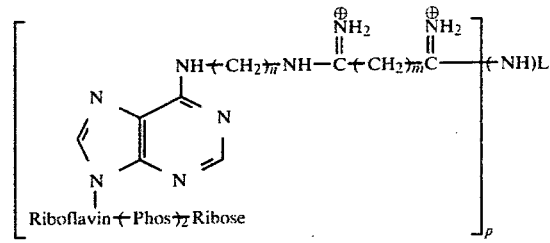

wherein Riboflavin—(Phos)₂̄Ribose represents the riboflavin-pyrophosphate-ribose residue in flavin adenine dinucleotide (FAD), —(NH)L is a protein or polypeptide (e.g., an immunoglobulin) bound through an amino group thereof, n is an integer from 2 through 10, m is an integer from 1 through 10, and p is on the average from 1 to the number of available amino groups in L. The FAD-labeled conjugates are useful as reagents in specific binding assays (e.g., immunoassays) to determine the conjugated protein or polypeptide, or a specific binding analog or partner thereof, in liquid media.

11 Claims, 1 Drawing Figure

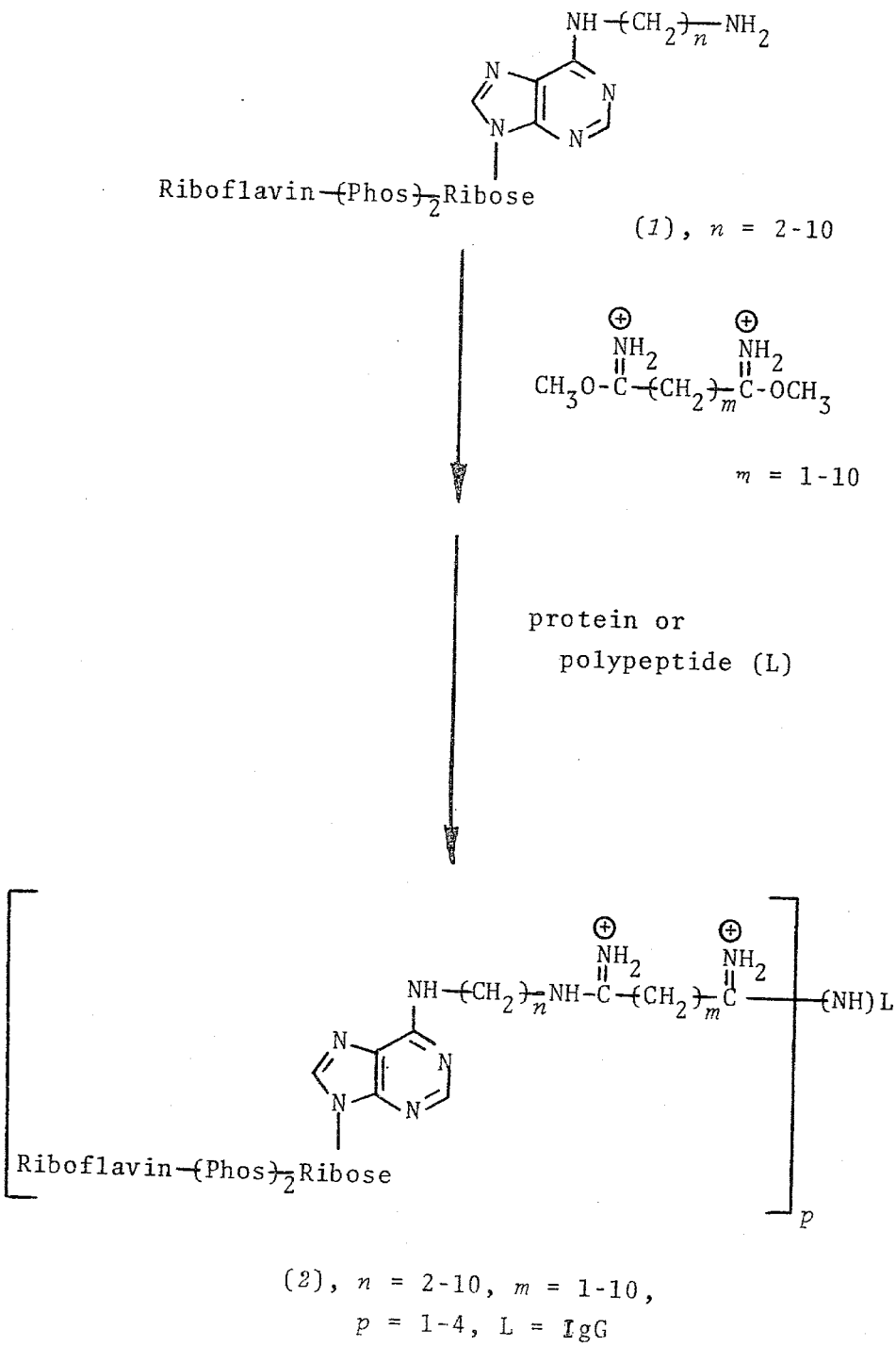
TABLE I

FLAVIN ADENINE DINUCLEOTIDE-LABELED PROTEIN AND POLYPEPTIDE CONJUGATES

BACKGROUND OF THE INVENTION

1. Field of the Invention

This invention relates to nonradioisotopically-labeled proteins and polypeptides useful as labeled conjugates in specific binding assays for determining such proteins and polypeptides, or specific binding partners thereof, in liquid media such as body fluids, particularly serum. In particular, the present invention relates to flavin adenine dinucleotide-labeled proteins (e.g., immunoglobulins) and polypeptides useful in nonradioisotopic immunoassays.

2. Description of the Prior Art

Specific binding assay methods have undergone a technological evolution from the original competitive binding radioimmunoassay (RIA) in which a radioisotope-labeled antigen is made to compete with antigen from a test sample for binding to specific antibody. In the RIA technique, sample antigen is quantitated by measuring the proportion of radioactivity which becomes associated with the antibody by binding of the radiolabeled antigen (the bound-species of the labeled antigen) to the radioactivity that remains unassociated from antibody (the free-species) and then comparing that proportion to a standard curve. A comprehensive review of the RIA technique is provided by Skelly et al, Clin. Chem. 19: 146(1973). While by definition RIA is based on the binding of specific antibody with an antigen or hapten, radiolabeled binding assays have been developed based on other specific binding interactions, such as between hormones and their binding proteins. All radiolabeled specific binding assays are by necessity heterogeneous, that is, the bound- and free-species of the labeled conjugate must be physically separated and the label (i.e., radioactivity) measured in one of the separated species.

From the radiolabeled binding assays have evolved nonradioisotopic binding assays employing labeling substances such as enzymes as described in U.S. Pat. Nos. 3,654,090 and 3,817,837. Recently, further improved nonradioisotopic binding assays have been developed as described in German Offenlegungschriften Nos. 2,618,419 and 2,618,511, based on U.S. Ser. Nos. 667,982 and 667,996, filed on Mar. 18, 1976 and assigned to the present assignee, employing particularly unique labeling substances, including coenzymes, cyclic reactants, cleavable enzyme substrates, and chemiluminescent molecules. Flavin adenin dinucleotide (FAD) is mentioned as being useful as a coenzyme label since FAD functions as a coenzyme in reactions which can be used to monitor specific binding reactions. The majority of the recently developed nonradioisotopic specific binding assays can be performed in a homogeneous format, that is, without separating the bound- and free-species of the labeled conjugate, due to the fact that the label expresses a different activity in the bound-species compared to the free-species.

In addition to its use as a coenzyme label, FAD has also been found to be useful as a prosthetic group label as described in U.S. Patent Applications Ser. Nos. 917,961 and 45,423, filed June 22, 1978 and June 4, 1979, respectively, both assigned to the present assignee. Various FAD-labeled ligand conjugates are described in the aforesaid applications. It is highly desirable to prepare FAD-labeled conjugates for proteins and polypeptides of clinical significance so as to enable the homogeneous, nonradioisotopic specific binding assay determination of such proteins and polypeptides, and their binding partners. Preparation of such labeled protein and polypeptide conjugates is complicated by the complex structure and heterogeneity of proteins and polypeptides; the molecular size, fragility, and susceptibility to denaturation of such ligands; the need to maintain water solubility in the labeled conjugates; the need to maintain proper configuration in the conjugated protein or polypeptide; and the expected instability of chemically modified proteins and polypeptides over long storage periods.

Flavin adenine dinucleotide (FAD) has the following chemical structure [*The Merck Index*, 9th ed. (1976) p. 532]:

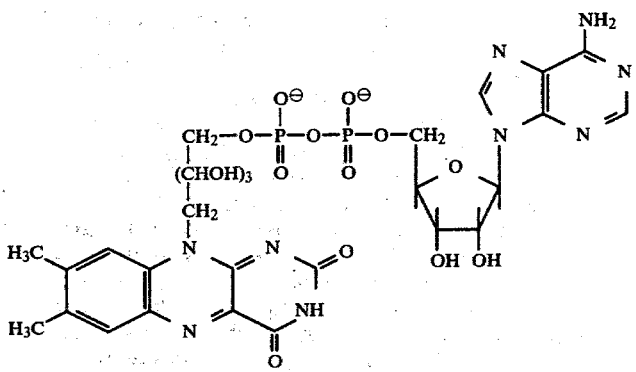

which hereinafter is abbreviated as:

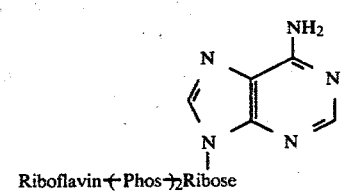

wherein Riboflavin-(-Phos₂)-Ribose represents the riboflavin-pyrophosphate-ribose residue in FAD.

The numerous conventional methods for modifying proteins and polypeptides and for coupling such ligands to solid supports and other materials are described in the following: for general reviews see *Methods in Enzymology*, vol. XLIV "Immobilized Enzymes", ed. Mosbach, Academic Press (New York 1976), *Affinity Chromatography*, Lowe and Dean, John Wiley and Sons (New York 1974), and *Clin. Chem.* 22:726(1976); and for specific references see *Science* 144:1344(1967) [the carbodiimide reaction], Erlanger et al, *Methods in Immunology and Immunochemistry*, ed. Williams and Chase, Academic Press (New York 1967), p. 149 [the mixed anhydride reaction], *Peptides and Amino Acids*, Kopple, W. A. Benjamin, Inc. (New York 1966) [the acid azide and active ester reactions], and *Proc. Nat. Acad. Sci. USA* 66:651(1970) [the bis-imidate reaction].

SUMMARY OF THE INVENTION

The present invention provides FAD-labeled proteins and polypeptides of the general formula:

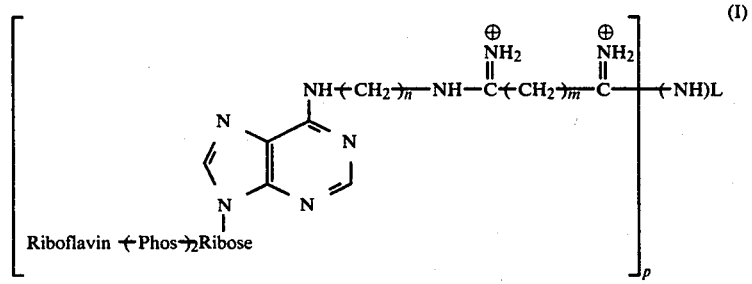

wherein $-(NH)L$ is a protein or polypeptide bound through an amino group thereof, n is an integer from 2 through 10, m is an integer from 1 through 10, and p is on the average from 1 through the number of available amino groups in L.

The present labeled conjugates are prepared by coupling the desired protein or polypeptide to flavin $N^6$-($\omega$-aminoalkyl)-adenine dinucleotides in the presence of bifunctional bis-imidates, as described in detail below. The labeled conjugates are used as reagents in the known homogeneous and heterogeneous specific binding assays, particularly immunoassays, employing FAD-labeled protein and polypeptide conjugates; are relatively well-characterizable due to the relative selectivity of the bis-imidate coupling technique, despite the heterogeneity of the functional groups on the ligands involved; and are sufficiently water soluble and stable to enable their use as assay reagents in commercial test kits.

DESCRIPTION OF THE PREFERRED EMBODIMENTS

The labeled conjugates (I) of the present invention are prepared by coupling the desired protein or polypeptide to flavin $N^6$-($\omega$-aminoalkyl)-adenine dinucleotides of the formula:

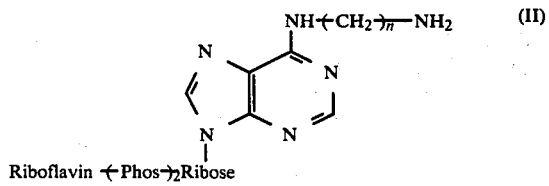

wherein n is as defined above, in the presence of a bifunctional bis-imidate of the general formula:

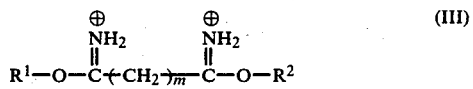

wherein m is as defined above and $R^1$ and $R^2$, which may be the same or different but which more usually are the same, are alkyl, preferably lower alkyl (i.e., having 1-4 carbon atoms) such as methyl, ethyl, n-propyl, isopropyl, and so forth. Particularly preferred bis-imidates (III) are the dimethyl alkylimidates, especially dimethyl adipimidate. The bis-imidates are generally available from commercial sources or may be prepared by published methods by those having ordinary skill in the art [Hunter and Ludwig, *J. Am. Chem. Soc.* 84:3491(1962)]. The bis-imidates will normally be provided in a suitable salt form which upon dissolution in the aqueous reaction media generates the positively charged bis-imidate species (III). Correspondingly, isolation of the labeled conjugate (I) from aqueous media such as by solvent evaporation or precipitation yields salt forms of the bis-imidates (III) wherein the counter anions to the protonated imino groups are taken from available anions in the media.

The coupling reaction is allowed to proceed in aqueous solution under mild conditions, e.g., at a pH between about 7 and about 10, more usually between 8 and 9, and at temperatures between about 0° C. and about 40° C., more usually between 20° C. and 30° C. Usually, the amino-functionalized FAD compounds (II), the bis-imidate (III), and the desired protein or polypeptide to be labeled are added in sequence, with a short incubation period for reaction between the amino-functionalized FAD and the bis-imidate of between 1 and 30 minutes, followed by addition of the protein or polypeptide and a second incubation period lasting between 10 minutes and 4 hours.

It has been generally found that the longer the second incubation period, the greater the degree of substitution of the FAD labeling moiety on the protein or polypeptide, i.e., the higher the value of p in formula (I). The upper limit on the number of FAD moieties that can be introduced to a given protein or polypeptide is theoretically limited only by the number of available amino groups in such protein or polypeptide. By available amino groups is meant those amino groups which are reactive with the bis-imidate coupling agent. Under the current state of knowledge, such amino groups comprise (a) the terminal α-amino groups of the peptide chain in the protein or polypeptide and (b) the ε-amino groups of lysyl residues occurring in the protein or polypeptide. The degree of substitution (i.e., the value of p) of the labeling moiety will vary between 1 and such theoretical upper limit depending on the characteristics desired for the labeled conjugate in the assay method contemplated. Normally, p will be on the average between 1 and 100, more usually between 1 and 20.

The aforementioned flavin $N^6$-($\omega$-aminoalkyl)-adenine dinucleotides (II) can be prepared as follows. 6-Chloro-$\beta$-D-ribofuranosylpurine is phosphorylated by treatment with phosphoryl chloride, yielding 6-chloropurine-5'-monophosphate, which upon reaction with $\alpha,\omega$-alkanediamines (wherein the alkylene chain is linear and comprises 2–10 carbons) produce $N^6$-($\omega$-aminoalkyl)-adenosine-5'-monophosphates [Trayer et al, *Biochem. J.* 139:609(1974)]. Continuing with the method of Trayer et al, the derivatized adenosine-5'-monophosphates are treated with ethyl trifluorothiolacetate to block the terminal $N^6$ amino group and with carbonyldiimidazole to block the phosphate group, yielding $N^6$-($\omega$-trifluoroacetamidoalkyl)-adenosine-5'-monophosphate imidazolides (see Example 1 hereinbelow). Reaction with riboflavin monophosphate in the presence of dimethylformamide, followed by threatment with base produces the desired $N^6$-($\omega$-aminoalkyl)-adenine dinucleotides.

The protein or polypeptide to be labeled according to the present invention will be antigenic, that is, capable of stimulating antibody production upon injection into a host animal, or, in the case of the smaller polypeptides, will be capable of being rendered antigenic by coupling to an appropriate carrier, such as albumin, as is well-known in the art. The range of molecular weights for the protein or polypeptide will usually be between 130 and 10,000,000, more usually between 1,000 and 1,000,000. Particular proteins and polypeptides may have widely varying biological functions, encompassing hormones, enzymes, transport proteins, receptor proteins, and immunoglobulins (e.g., antibodies). All proteins and polypeptides of clinical significance are contemplated for labeling according to the present invention since any particular protein or polypeptide will have available (e.g., a terminal $\alpha$-amino group or a lysyl $\epsilon$-amino group), or can be modified to make available, an amino group for coupling to the FAD moiety by the bis-imidate technique. An amino-functionalized derivative of a protein or polypeptide of clinical significance will of course still be considered a protein or polypeptide in a true sense and in accordance with the use of such terms herein. Moreover, proteins and complex polypeptides (a polypeptide is conventionally defined as a polymer of amino acids joined by amide linkages, forming chains that can consist of as few as two or as many as several thousand amino acid residues) will contain several terminal $\alpha$-amino groups available for coupling. Furthermore, it is understood that substantially all proteins and most polypeptides contain one or more lysyl residues, making available $\epsilon$-amino groups thereof for coupling. Accordingly, proteins and polypeptides as a class can be labeled in the manner of the present invention and used as labeled conjugates in specific binding assays.

Particular polypeptides that can be labeled according to the present invention are angiotensin I and II, C-peptide, oxytocin, vasopressin, neurophysin, gastrin, secretin, glucagon, bradykinin and relaxin. Proteins contemplated by the present invention include the classes of protamines, mucoproteins, glycoproteins, globulins, albumins, sclero-proteins, phosphoproteins, histones, lipoproteins, chromo-proteins, and nucleoproteins. Examples of specific proteins are prealbumin, $\alpha_1$-lipoprotein, human serum albumin, $\alpha_1$-acid glycoprotein, $\alpha_1$-antitrypsin, $\alpha_1$-glycoprotein, transcortin, thyroxine binding globulin, haptoglobin, hemoglobin, myoglobin, ceruloplasmin, $\alpha_2$-lipoprotein, $\alpha_2$-macroglobulin, $\beta$-lipoprotein, erythropoietin, transferin, homopexin, fibrinogen, the immunoglobulins such as IgG, IgM, IgA, IgD, and IgE, and their fragments, e.g., $F_c$ and $F_{ab}$, complement factors, prolactin, blood clotting factors such as fibrinogen, thrombin and so forth, insulin, melanotropin, somatotropin, thyrotropin, follicle stimulating hormone, leutinizing hormone, gonadotropin, thyroid stimulating hormone, placental lactogen, intrinsic factor, transcobalamin, serum enzymes such as alkaline phosphatase, lactic dehydrogenase, amylase, lipase, phosphatases, cholinesterase, glutamic oxaloacetic transaminase, glutamic pyruvic transaminase, and uropepsin, endorphins, enkephalins, protamine, tissue antigens, bacterial antigens, and viral antigens such as hepatitis associated antigens (e.g., $HB_sAg$, $HB_cAg$ and $HB_eAg$).

Labeled protein and polypeptide conjugates prepared according to the present invention have been found to be of relatively well-characterizable structure due to the relative selectivity of the bis-imidate coupling reaction despite the heterogeneity of the functional groups on the proteins and polypeptides involved. Reproducibility in the synthesis of the complex conjugates permits their controlled manufacture on a large scale for incorporation in commercial test kits. The conjugates serve as useful reagents in homogeneous specific binding assays, it having been confirmed that even where the labeled material is a high molecular weight protein (e.g., an immunoglobulin), the activity of the FAD-labeled conjugates is significantly altered upon binding with antibody to the protein. Sufficient water solubility and stability is exhibited by the conjugates to permit their use in commercial test kits. Of particular note is the fact that the presence of positively charged imino groups in the labeled conjugates is understood to greatly assist maintenance of proper conformation of the labeled protein or polypeptide.

The present invention will now be illustrated, but is not intended to be limited, by the following examples.

EXAMPLE 1

Preparation of FAD-labeled IgG

The conjugates are prepared according to the reaction sequence shown in Table 1 in the drawing. This synthetic route is exemplified by the following method of preparing labeled conjugate (2) wherein n=6, m=4, p is on the average between 1 and 4, and the protein or polypeptide labeled is immunoglobulin G (IgG).

Flavin $N^6$-(6-aminohexyl)-adenine dinucleotide (1)

$N^6$-(6-Trifluoroacetamidohexyl)-adenosine-5'-monophosphate was synthesized by reacting 6-chloropurine-5'-monophosphate with 1,6-hexanediamine according to the method of Trayer et al, *Biochem J.* 139:609(1974).

Fifty-six milligrams (mg) of $N^6$-(6-trifluoroacetamidohexyl)-adenosine-5'-monophosphate (0.1 mmol) was dissolved in about 10 milliliters (ml) of water and 25 microliters ($\mu$l) of tri-n-butylamine (0.1 mmol) was added. The water was removed under vacuum and the residue was dissolved in 10 ml of dry dimethylformamide (DMF) which was then removed under vacuum. The residue was evaporated from dry DMF three more times. The final residue was dissolved in 10 ml of dry DMF. Eighty milligrams of N,N'-carbonyldiimidazole (0.5 mmol) was added and allowed to react for 1.5 hours. Then 15 μl of water was added and the solvent was removed under vacuum. The residue [N$^6$-(6-trifluoroacetamidohexyl)-adenosine-5'-monophosphate imidazolide] was dissolved in 10 ml of DMF.

Forty-seven milligrams of riboflavin-5'-monophosphate (0.1 mmol) was dissolved in about 10 ml of water and added dropwise to 20 ml of acetone containing 43 μl of tri-n-octylamine (0.1 mmol). A precipitate formed before the addition was complete. The solvent was removed with a rotary evaporator until the riboflavin-5'-monophosphate dissolved. Then 5 ml of acetone and 5–10 ml of DMF were added and the mixture was taken to dryness. The residue was dissolved in 15–20 ml of dry DMF and taken to dryness (this process was repeated three times). The residue was dissolved in 5 ml of DMF and combined with the above-mentioned 10 ml solution of the imidazolide in DMF.

The reaction mixture was allowed to stand at room temperature overnight and then the solvent was removed. The residue was taken up in 50 ml of water and applied to a 2.5×25 centimeter (cm) column of DEAE-cellulose in the bicarbonate form (Whatman DE23, Reeve Angel, Clifton, N.J. USA). The chromatogram was developed with a linear gradient generated with 2 liters (L) of water and 2 L of 0.3 molar (M) ammonium bicarbonate (23 ml fractions were collected). Thin-layer chromatography on silica gel 60 F254 (E. Merck, Darmstadt, West Germany) using a 7:3 volume:volume (v:v) mixture of ethanol—1 M triethylammonium bicarbonate (pH 7.5) showed that fractions numbered 68 to 73 contained major ($R_f$=0.75) and minor ($R_f$=0.36) yellow compounds. These fractions were pooled and the optical absorption spectrum had maxima at 267, 373 and 450 nanometers (nm).

The solvent was removed from the pooled material and the residue was dissolved in about 5 ml of water. This solution was adjusted to pH 11.0 with 5 N sodium hydroxide and allowed to stand at room temperature for nine hours. Thin-layer chromatography showed that the component with $R_f$=0.75 disappeared while a new yellow material with $R_f$=0.37 appeared. The reaction mixture was adjusted to pH 8.0 with hydrochloric acid and applied to a 2.5×20 cm column of DEAE-cellulose in the bicarbonate form. The chromatogram was developed with a linear gradient developed with 1 L of water and 1 L of 0.2 M ammonium bicarbonate. The yellow effluent from the column was pooled and the solvent was removed. The residue was adsorbed onto 2 grams (g) of silica gel which was placed atop a 50 g column of silica gel equilibrated with a 8:2 (v:v) mixture of ethanol—1 M triethylammonium bicarbonate (pH 7.5). The column was eluted with an 8:2 (v:v) mixture of ethanol—1 M triethylammonium bicarbonate (pH 7.5), the yellow component with $R_f$=0.37 was collected, and the solvent was removed. The yield of flavin N$^6$-aminohexyl-adenine dinucleotide in the residue was about 10% based on absorbance at 450 nm.

Flavin adenine dinucleotide-labeled IgG (2)

To 4.24 mg flavin N$^6$-(6aminohexyl)-adenine dinucleotide, prepared as described above, was added 2.5 mg dimethyl adipimidate dihydrochloride (Pierce Chemical Co., Rockford, IL. USA) in 1 ml of water and 5 μl of triethylamine. The reaction was stirred at room temperature for 10 minutes and 40 milligrams (mg) human immunoglobulin G (IgG) [Miles Laboratories, Inc., Elkhart, Ind. USA] in 1 ml of 0.1 M sodium pyrophosphate buffer (pH 8.5) was then added. After further stirring at room temperature for 3 hours, the reaction mixture was applied to a 2.5×50 cm G-25 Sephadex (Pharmacia Fine Chemicals, Uppsala, Sweden) column equilibrated and eluted with 0.1 M sodium phosphate buffer (pH 7.0). Fractions from the first eluting peak having absorbance at 450 nm were collected and dialyzed successively against 4 L of 0.1 M sodium phosphate buffer (pH 7.0) for 16 hours, 4 L of 0.1 M sodium phosphate buffer (pH 7.0) containing 1 M sodium chloride for 24 hours, and 0.01 M sodium phosphate buffer (pH 7.0) for 48 hours. Sodium azide was then added to 0.1% weight:volume (w:v). The reaction material was filtered through a 0.22 micron (μ) Millipore filter and stored.

The above described synthesis of the FAD-labeled conjugate (2), n=6, m=4, can be modified to yield labeled conjugates wherein n=2–10 and m=1–10 by replacing the starting materials 1,6-hexanediamine and dimethyl adipimidate, respectively, with the appropriate α,ω-alkanediamine and dimethyl alkyldiimidate as follows:

| n | αω-alkanediamine |
|---|---|
| 2 | ethylenediamine |
| 3 | 1,3-propanediamine |
| 4 | 1,4-butanediamine |
| 5 | 1,5-pentanediamine |
| 7 | 1,7-heptanediamine |
| 8 | 1,8-octanediamine |
| 9 | 1,9-nonanediamine |
| 10 | 1,10-decanediamine |

| m | dimethyl alkylimidate |
|---|---|
| 1 | dimethyl malonimidate |
| 2 | dimethyl succinimidate |
| 3 | dimethyl glutarimidate |
| 5 | dimethyl pimelimidate |
| 6 | dimethyl octanediimidate |
| 7 | dimethyl nonanediimidate |
| 8 | dimethyl decanediimidate |
| 9 | dimethyl undecanediimidate |
| 10 | dimethyl dodecanediimidate |

EXAMPLE 2

Preparation of Apoglucose Oxidase

An aliquot of purified glucose oxidase with low catalase activity obtained from the Research Products Division of Miles Laboratories, Inc., Elkhart, Ind. USA, containing 81.4 mg of enzyme was added to 6 ml anhydrous glycerol and cooled to 0° C. The pH of the reaction was adjusted to 1.4 with 10% sulfuric acid. After stirring at 0° C. for two hours, the reaction was chromatographed at 5° C. on a column of Sephadex G-50, coarse, (Pharmacia Fine Chemicals, Inc., Piscataway, N.J. USA) which had been equilibrated with 30% glycerol, pH 1.4 (flow rate approx. 120 ml/hr). The apoenzyme was eluted with 30% glycerol, pH 1.4. The protein peak determined by absorbance at 280 nm was pooled and a bovine serum albumin/charcoal suspension containing 200 mg bovine serum albumin and 600 mg charcoal (RIA grade from Schwarz-Mann, Orangeburg, N.Y. USA) in 4.9 ml of 0.4 M sodium phosphate buffer, pH 8.0, was added. The pH was adjusted to pH 7.0; and after stirring for one hour at 0° C., the mixture was passed successively through 0.8μ and 0.22μ Millipore filters (Millipore Corp., Bedford, Mass. USA) mounted in Sweenex filter apparatus (Millipore Corp.)

on 50 ml disposable syringes. Sodium azide was added to the solution of apoenzyme to give a concentration of 0.1% and the solution was stored at 4° C.

EXAMPLE 3

Determination of Antibody to IgG

The reagents used in the assay were as follows:

| Reagent | Composition |
|---------|-------------|
| A | 0.1 M sodium phosphate buffer (pH 7.0) |
| B | 10 mM 4-aminoantipyrine |
| C | 1.0 M glucose |
| D | 25 mM 3,5-dichloro-2-hydroxybenzene sulfonate in Reagent A |
| E | 1.2 mg/ml horseradish peroxidase in Reagent A |
| F | 30% (w:v) bovine serum albumin (Research Products Division, Miles Laboratories, Inc., Elkhart, Indiana USA) |
| G | FAD-labeled IgG conjugate in solution (see Example 1) |
| H | apoglucose oxidase (see Example 2) |
| I | rabbit antiserum against human IgG (obtained from Behring Diagnostics, Somerville, New Jersey USA) |
| J | standards - human IgG in Reagent A at predetermined levels |

Reagent mixes were prepared as follows:

Mix #1—180 μl Reagent A, 20 μl Reagent B, 100 μl Reagent D and 5 μl Reagent G (5.4 μM)

Mix #2—0.3 ml total volume of various proportions containing the volume of Reagent I indicated in Table 2 below with the remaining volume being made up of Reagent A Mix #3—80 μl Reagent D, 50 μl Reagent E, 33 μl Reagent F, 137 μl Reagent A and 1.6 μl Reagent H (4.2 μN FAD-binding sites)

To 300 μl of Mix #1 was added 300 μl of Mix #2 and 300 μl of Reagent A in separate reaction cuvettes. After at least 10 minutes incubation at room temperature, 300 μl of Mix #3 was added to each reaction. After further incubation for 30 minutes at 20° C., the absorbance at 520 nm was measured in each cuvette. The results were as follows:

TABLE 2

| Volume of antiserum added to prepare Mix #2 (μl) | Absorbance (520 nm) |
|---|---|
| 0 | 0.859 |
| 2 | 0.750 |
| 4 | 0.602 |
| 6 | 0.494 |
| 8 | 0.443 |
| 10 | 0.415 |
| 12 | 0.408 |
| 14 | 0.392 |
| 16 | 0.375 |

The results demonstrate that as antibody level increases, the glucose oxidase activity generated by the FAD label conjugated to IgG decreases.

EXAMPLE 4

Assay for IgG

These reactions were carried out using the reagents described in Example 3 above. Designated levels of human IgG in 300 μl volumes of Reagent A were combined with Mix #1 in separate reaction cuvettes. Then a mixture of 12 μl of Reagent I and 288 μl of Reagent A was added to each reaction. After 10 minutes 300 μl of Mix #3 was added and the reaction mixtures incubated at 20° C. for 30 minutes. At the end of this period, the absorbance at 520 nm was measured in each cuvette. The results were as follows:

TABLE 3

| Amounts of Human IgG Added (μg) | Absorbance (520 nm) |
|---|---|
| 0 | 0.579 |
| 4 | 0.653 |
| 8 | 0.751 |
| 12 | 0.844 |
| 16 | 0.986 |
| 24 | 1.06 |

Thus, it was demonstrated that the present invention provides labeled proteins useful as reagents in specific binding assays.

What is claimed is:

1. A flavin adenine dinucleotide-labeled conjugate of the formula:

$$\left[ \begin{array}{c} \text{Riboflavin}\text{-}(\text{Phos})_2\text{-}\text{Ribose} \end{array} \middle| \text{NH-(CH}_2)_{\overline{n}}\text{NH-}\overset{\overset{\oplus}{N}H_2}{\underset{\|}{C}}\text{-(CH}_2)_{\overline{m}}\overset{\overset{\oplus}{N}H_2}{\underset{\|}{C}}\text{-----(NH)L} \right]_p$$

wherein Riboflavin -(-Phos-)-2 Ribose represents the riboflavin-pyrophosphate-ribose residue in flavin adenine dinucleotide, -(-NH)L is a protein or polypeptide bound through an amino group thereof whereby said protein or polypeptide in the conjugate is capable of being bound by an antibody, n is an integer from 2 through 10, m is an integer from 1 through 10, and p is on the average from 1 to the number of available amino groups in L.

2. The conjugate of claim 1 wherein -(-NH)L is a protein or polypeptide of molecular weight between 130 and 10,000,000.

3. The conjugate of claim 1 wherein -(-NH)L is a protein or polypeptide of molecular weight between 1,000 and 1,000,000.

4. The conjugate of claim 1 wherein -(-NH)L is an immunoglobulin.

5. The conjugate of claim 4 wherein said immunoglobulin is IgG.

6. The conjugate of claim 4 wherein said immunoglobulin is IgM.

7. The conjugate of claim 4 wherein said immunoglobulin is IgA.

8. The conjugate of any of claims 1-7 wherein p is on the average from 1 to 100.

9. The conjugate of any of claims 1-7 wherein p is on the average from 1 to 20.

10. The conjugate of claim 9 wherein n=6 and m=4.

11. The conjugate of any of claims 1-7 wherein n=6 and m=4.

* * * * *